US00PP13614P2

(12) United States Plant Patent
Moolenaar

(10) Patent No.: US PP13,614 P2
(45) Date of Patent: Mar. 4, 2003

(54) BEGONIA PLANT NAMED 'PLA0002BEG'

(75) Inventor: Alfred Nicol Moolenaar, Voorhout (NL)

(73) Assignee: Genplant B.V., Voorhout (NL)

( * ) Notice: Subject to any disclaimer, the term of this patent is extended or adjusted under 35 U.S.C. 154(b) by 0 days.

(21) Appl. No.: 09/905,965

(22) Filed: Jul. 17, 2001

(51) Int. Cl.[7] ..... A01H 5/00
(52) U.S. Cl. ..... Plt./343
(58) Field of Search ..... Plt./343

*Primary Examiner*—Bruce R. Campell
*Assistant Examiner*—Annette H. Para
(74) *Attorney, Agent, or Firm*—Foley & Lardner

(57) ABSTRACT

A distinct begonia plant named 'PLA0002BEG' characterized by its red/purple-eyed leaves. This Begonia is commercially grown for its leaves, its flowers are small and short lasting. The flowers of the parent germplasm grow far above the leaf, in contrast to the flowers of 'PLA0002BEG' which grow beneath the leaf. 'PLA0002BEG' grows much more compact and fuller, has much smaller leaves than the parent germplasm, and is homogenous.

2 Drawing Sheets

LATIN NAME OF THE GENUS AND SPECIES OF THE PLANT CLAIMED

*Begonia conchifolia*.

VARIETY DENOMINATION

'PLA0002BEG'.

BACKGROUND OF THE INVENTION

The present invention comprises a new and distinct cultivar of begonia plant, botanically known as *Begonia conchifolia*, and hereinafter referred to by the cultivar name 'PLA0002BEG'.

The new cultivar was discovered by the inventor, Alfred Nicol Moolenaar in Voorhout, The Netherlands in 1998. The new cultivar was obtained by careful selection from the parent germplasm followed by further evaluations of its characteristics. 'PLA0002BEG' is a natural mutation from the cultivar *Begonia conchifolia*.

The new cultivar was first asexually propagated in Voorhout, The Netherlands, in early 1999 by the inventor. Subsequent asexual reproduction of the new cultivar by means of vegetative cuttings has demonstrated that the combination of characteristics as herein disclosed for the new cultivar are firmly fixed and retained through successive generations of asexual reproduction.

The new cultivar 'PLA0002BEG' has not been observed under all possible envirnmental conditions. The phenotype of the new cultivar may vary significantly when grown under different conditions of temperature, light intensity and day length without any change in genotype.

BRIEF SUMMARY OF THE INVENTION

The following characteristics have been repeatedly observed and distinguish begonia 'PLA0002BEG' from other begonias commercially known and used in the floriculture industry:

1. Flowers of 'PLA0002BEG' stay below the leaves;

2. More compact and fuller growth habit than other known begonia varieties;

3. Significantly smaller leaves than other known begonia varieties;

4. Homogenous; and

5. Striking red/purple-eyed leaves.

Of the many commercial cultivars known to the present inventor, the most similar in comparison to 'PLA0002BEG' is the cultivar *Begonia conchifolia*, an unpatented botanical cultivar. The flowers of the parent germplasm grow far above the leaf in contrast to the flowers of 'PLA0002BEG' which stay below the leaves. 'PLA0002BEG' has a more compact and fuller growth habit and much smaller leaves the parent germplasm. 'PLA0002BEG' is homogenous (stable), whereas the parent germplasm is not.

The new cultivar 'PLA0002BEG' is principally distinguishable from other begonia varieties by compact and full growth habit, small leaves, small flower stems, and striking red/purple-eyed leaves.

BRIEF DESCRIPTION OF THE DRAWINGS

The accompanying photographic drawings of 'PLA0002BEG' were taken on Jan. 30, 2001, in Rijswijk, The Netherlands.

Sheet 1 shows the commercial size and form of 'PLA0002BEG'.

Sheet 2 is close up of the leaf.

DETAILED BOTANICAL DESCRIPTION

The following observations, measurements and values describe plants grown in Voorhout, the Netherlands under greenhouse conditions which closely approximate those generally used in commercial practice. Color references are made to The Royal Horticultural Society Colour Chart (R.H.S.), except where general colors of ordinary significance are used.

Propagation:

*Type cutting*.—Vegetative cutting.

*Rooting time*.—21 days in 19 degrees Celsius average day/night temperature.

*Rooting habit*.—Rhizomatous.

*Time for shoot development*.—5 to 6 weeks after cutting in 19 degrees Celsius average day/night temperature.

Growing conditions:

*Temperature*.—19 degrees Celsius.

*Photoperiodic treatments*.—None.

*Growth retardation*.—Fertilizer is added to make 'PLA0002BEG' grow more compact.

Plant description: The following description is based on observations taken on 3 month old plants grown in 13 cm pots.

*Form*.—Rosette.

*Height*.—20 cm.

*Width*.—8 cm; area of spread is approximately 30 cm.

*Branching*.—No branching.

*Vigor*.—Vigorous, producing plants approximately 13 weeks after cutting.

*Cold/drought tolerance*.—Tolerance to 10–11 degrees Celsius; approximately 60% less water is needed than a *Begonia rex*.

Foliage:

*Color*.—Upper side young leaf: Green RHS 144 A with red/purple eye RHS 85 A. Under side young leaf: Green RHS 147 C. Upper side mature leaf: Dark green RHS 139 A with red/purple eye RHS 59 A. Under side mature leaf: Green RHS 148 C with red/purple at underside of eye RHS 59 C (around the end of the petiole) and some parts of veins.

*Veination*.—Young leaf upper side: Brown RHS 174 A. Young leaf under side: Brown RHS 174 A. Mature leaf upper side: Green RHS 139D, parts are red/purple RHS 59 C. Mature leaf under side: Green RHS 48 A, pars are red/purple RHS 59A.

*Shape*.—Ovate with mucranulate tip and round base.

*Size*.—10–11 cm length, 8 cm width.

*Margin*.—Crenulate.

*Tip*.—Mucranulate.

*Attachment*.—Peltate.

*Texture*.—Glabrous.

Inflorescence:

*Natural flowering season*.—Spring.

*Flower longevity*.—Short, 3–4 day lastingness of the bloom.

*Bud description*.—Rather flat with bulbous center that houses the reproductive organs, heart shaped, up to 7 mm wide and 6 mm tall, color is pure white with pinkish edge; yellow reproductive organs shine through the wand.

Petals:

*Male flower*.—Number: 2. Color: Pure white or white and pink RHS 65 A edges fading to white towards the center. Form: Heart-shaped. Size: 7 mm wide and 7 mm high. Margin: Entire.

*Female flower*.—Number: 4 to 5. Color: Upper and under side of the two tepals above the ovary: pure white and pink RHS 64 C edges fading to white towards the center. Upper and under side of the two or three tepals under the three sided receptacle: Pure white with dark pink edge RHS 64 C. Form: Heart-shaped tip is praemorse. Size: 7 mm wide and 6 mm high. Margin: Upper tepals are entire, lower tepals are entire with serrate tip.

*Receptacle*.—Shape: Triquetrous. Color: White with pinkish glare like petals. Size: 10 mm wide and 7 mm high. Position: Located between the upper and lower petals.

Reproductive organs:

*Ovary*.—Color: Green RHS 145 C. Size: Length 1 cm, width 2 mm.

*Pistil*.—Amount: 3. Color: Yellow RHS 7 A. Size: Length 4 mm.

*Stamen*.—Amount: Up to twenty. Shape: Tubular. Size: Length 3 mm, width 0.8 mm, height 1.2 mm. Color: Yellow RHS 7 A.

*Seed/fruit*.—Not produced.

Resistance to pests and disease: Free of mites, slightly sensitive to lice, rather resistant to bacteria, good resistance against fungus.

General observations: 'PLA0002BEG' needs to be shadowed lightly in the summer to avoid damage from bright sunlight. Lowest temperature tolerance is 14 degrees Celsius, highest temperature tolerance is 26 degrees Celsius.

I claim:

1. A new and distinct cultivar of begonia plant named 'PLA0002BEG' as described and illustrated.

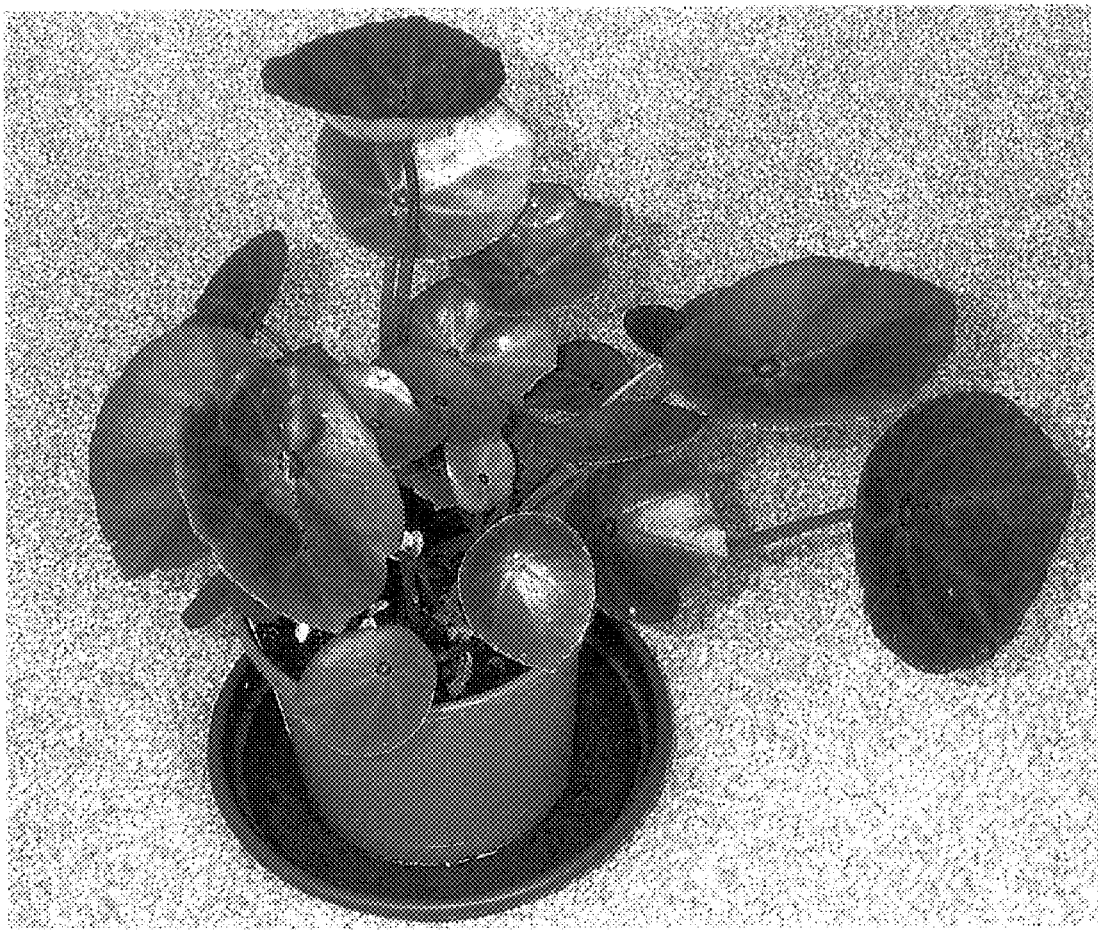

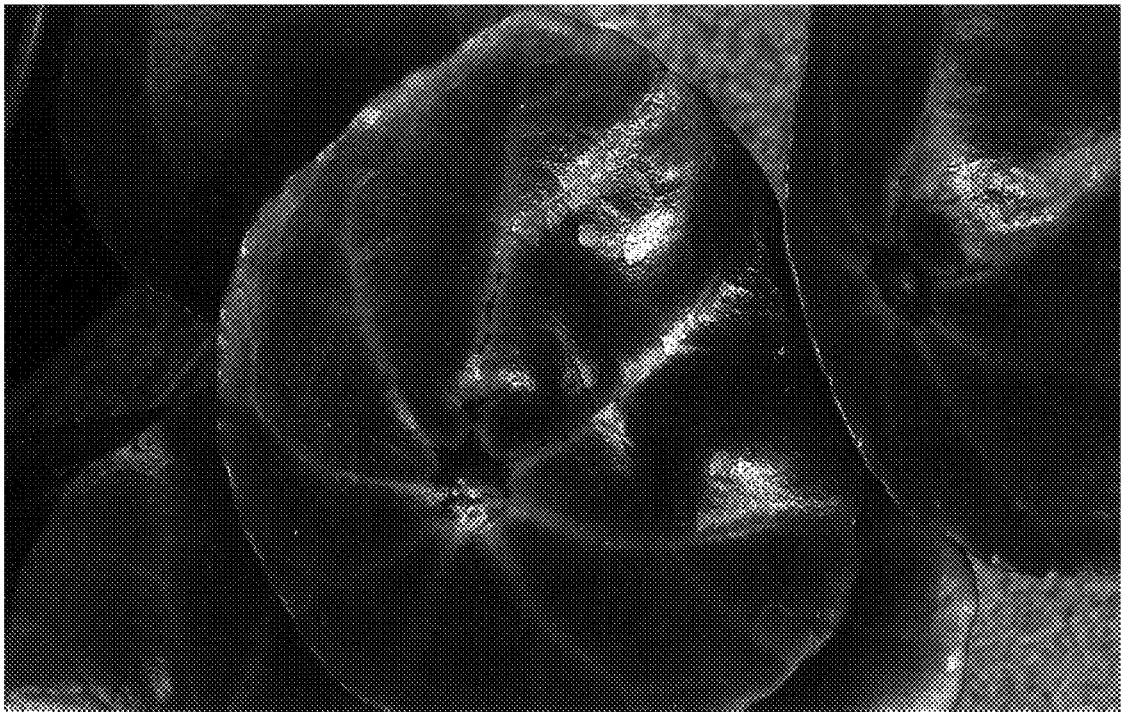

* * * * *